(12) United States Patent
Ehret

(10) Patent No.: US 12,064,519 B1
(45) Date of Patent: Aug. 20, 2024

(54) VAPORIZATION TABLET

(71) Applicant: Christian Ehret, Pittsburgh, PA (US)

(72) Inventor: Christian Ehret, Pittsburgh, PA (US)

(73) Assignee: GELLY LLC, Pittsburgh, PA (US)

( * ) Notice: Subject to any disclaimer, the term of this patent is extended or adjusted under 35 U.S.C. 154(b) by 140 days.

(21) Appl. No.: 17/190,948

(22) Filed: Mar. 3, 2021

Related U.S. Application Data

(60) Provisional application No. 62/984,807, filed on Mar. 4, 2020.

(51) Int. Cl.
| | |
|---|---|
| *A61K 31/05* | (2006.01) |
| *A61K 9/20* | (2006.01) |
| *A61K 9/24* | (2006.01) |
| *A61K 31/352* | (2006.01) |
| *A61K 45/06* | (2006.01) |
| *A61M 15/00* | (2006.01) |

(52) U.S. Cl.
CPC ............ *A61K 9/209* (2013.01); *A61K 9/2095* (2013.01); *A61K 31/05* (2013.01); *A61K 31/352* (2013.01); *A61K 45/06* (2013.01); *A61M 15/0028* (2013.01)

(58) Field of Classification Search
CPC ...... A61K 9/209; A61K 9/2095; A61K 31/05; A61K 31/352; A61K 45/06; A61K 15/0028
See application file for complete search history.

(56) References Cited

U.S. PATENT DOCUMENTS

2019/0192810 A1 * 6/2019 Trzecieski ........... A61M 11/003

FOREIGN PATENT DOCUMENTS

| WO | WO-2013098402 A1 * | 7/2013 | ........... A61K 31/137 |
| WO | WO-2018044895 A1 * | 3/2018 | ........... A61K 31/135 |
| WO | WO-2020150616 A1 * | 7/2020 | ............. A61K 31/07 |

OTHER PUBLICATIONS

Andre et al. (Front. Plant Sci. 2016; 7(19): 17 pages) (Year: 2016).*
Bennett, P. (THCA and CBD Crystalline: Cannabinoids at Their Purest [online] retrieved from https://www.leafly.com/news/strains-products/what-are-thca-cbda-crystalline-cannabinoids; 2018: 8 pages). (Year: 2018).*
Collins English Dictionary [online] retrieved on Aug. 8, 2023 from: Surrounding definition and meaning | Collins English Dictionary (collinsdictionary.com); 2 pages. (Year: 2023).*

* cited by examiner

*Primary Examiner* — Ernst V Arnold

(57) ABSTRACT

Disclosed is a vaporization tablet including an inner core comprising a first cannabis concentrate, the first cannabis concentrate comprising terpenes, and an outer layer at least partially surrounding the inner core, the outer layer comprising at least one of THCA and CBDA.

20 Claims, 1 Drawing Sheet

VAPORIZATION TABLET

CROSS-REFERENCE TO RELATED APPLICATIONS

This application claims priority to U.S. Provisional Application No. 62/984,807, filed Mar. 4, 2020, entitled "SOLVENTLESS EXTRACTS, VAPORIZER CARTRIDGES, AND METHODS FOR MAKING THE SAME," the content of which is incorporated by reference herein in its entirety.

BACKGROUND

Field

This disclosure relates generally to cannabis concentrates and, in particular, a vaporization tablet and method for making the same.

Technical Considerations

Cannabis concentrates can be difficult to dose and consume. Users often must use specialized tools to remove a dose of concentrate from a container and to place it in a vaporization device for consumption. The concentrate is often sticky and resinous, making it difficult to separate and dose. For medical applications, patients are unable to consistently dose concentrates due to differences in densities and forms.

SUMMARY

According to non-limiting embodiments, provided is a vaporization tablet, comprising: an inner core comprising a first cannabis concentrate, the first cannabis concentrate comprising at least one terpene; and an outer layer at least partially surrounding the inner core, the outer layer comprising at least one of THCA and CBDA.

In non-limiting embodiments, the first cannabis concentrate further comprises at least one of the following cannabinoids: THC, THCA, THCV, CBD, CBDA, CBG, CBGA, CBN, CBNA, CBC, CBCA, CBDV, or any combination thereof. In non-limiting embodiments, at least one of the first cannabis concentrate and the second cannabis concentrate comprises a predetermined dose of at least one cannabinoid. In non-limiting embodiments, the outer layer comprises a second cannabis concentrate, the second cannabis concentrate comprising the at least one of THCA and CBDA. In non-limiting embodiments, the outer layer is crystalized. In non-limiting embodiments, the outer layer comprises compressed crystals and/or powder of THCA and/or CBDA. In non-limiting embodiments, a terpene content of the outer layer is less than 1% by weight, and a terpene content of the inner core is greater than 1% by weight. In non-limiting embodiments, at least 95% by weight of the outer layer consists of at least one of THCA and CBDA. In non-limiting embodiments, the outer core comprises a second cannabis concentrate, the second cannabis concentrate having a firmer consistency than the first cannabis concentrate.

According to non-limiting embodiments, provided is a vaporization tablet, comprising: an inner core comprising a first cannabis concentrate; and an outer layer comprising a second cannabis concentrate, the outer layer surrounding the inner core.

In non-limiting embodiments, the inner core comprises at least one terpene, and the outer layer comprises at least one cannabinoid. In non-limiting embodiments, the outer layer comprises at least one of THCA and CBDA. In non-limiting embodiments, the first cannabis concentrate comprises a predetermined dose of at least one cannabinoid. In non-limiting embodiments, the vaporization tablet further comprises a surface layer surrounding the outer layer, the surface layer comprising a vaporizable material.

According to non-limiting embodiments, provided is a product comprising a plurality of tablets, each tablet comprising an inner core and an outer layer, wherein at least one of the inner core and the outer layer comprises a dose of at least one cannabinoid, wherein the dose of each tablet is substantially the same.

In non-limiting embodiments, each tablet is substantially spherical. In non-limiting embodiments, the inner core of each tablet comprises a first cannabis concentrate includes at least one cannabinoid and one terpene, and the outer layer of each tablet comprises a second cannabis concentrate including at least one of the following: THCA, CBDA, CBGA, CBNA, CBCA, or any combination thereof. In non-limiting embodiments, a terpene content of the outer layer is less than 1% by weight, and a terpene content of the inner core is greater than 1% by weight. In non-limiting embodiments, the outer layer consists essentially of at least one cannabinoid in acidic form. In nonlimiting embodiments, a first subset of the plurality of tablets comprise an inner core including a first set of terpenes, and a second subset of the plurality of tablets comprise an inner core including a second set of terpenes.

According to non-limiting embodiments, provided is a method for making vaporization tablets, including: extracting a first cannabis concentrate from cannabis plant matter; extracting a second cannabis concentrate from the cannabis plant matter; and forming a tablet from the first cannabis concentrate and the second cannabis concentrate, wherein the tablet comprises an inner core and an outer layer, the inner core comprising the first cannabis concentrate and the outer core layer comprising the second cannabis concentrate.

In non-limiting embodiments, the outer layer is firmer than the inner core. For example, the outer layer may be less malleable, viscous, or pliable than the inner core. In non-limiting embodiments, the second cannabis concentrate comprises THCA and/or CBDA, and wherein the first cannabis concentrate comprises terpenes. In non-limiting embodiments, the second cannabis concentrate comprises terpenes, and wherein the first cannabis concentrate comprises THCA and/or CBDA. In non-limiting embodiments, extracting the first cannabis concentrate comprises distilling terpenes from the cannabis plant matter, and wherein extracting the second cannabis plant matter comprises processing the cannabis plant matter with at least one solvent. In non-limiting embodiments, extracting the second cannabis plant matter comprises processing the cannabis plant matter with at least one of cold water and ice.

These and other features and characteristics of the vaporization tablets disclosed herein, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

Additional advantages and details are explained in greater detail below with reference to the exemplary embodiments that are illustrated in the accompanying schematic figures, in which.

DESCRIPTION

Figure 1:
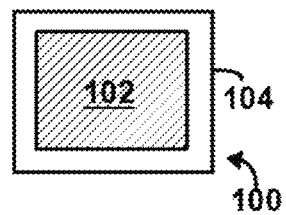
FIG. 1 is a diagram of a vaporization tablet according to a non-limiting embodiment.

For purposes of the description hereinafter, the terms "end", "upper", "lower", "right", "left", "vertical", "horizontal", "top", "bottom", "lateral", "longitudinal" and derivatives thereof shall relate to the subject matter as it is oriented in the drawing figures. However, it is to be understood that the subject matter may assume various alternative variations and step sequences, except where expressly specified to the contrary. It is also to be understood that the specific devices and processes illustrated in the attached drawings, and described in the following specification, are simply exemplary embodiments or aspects of the subject matter. Hence, specific dimensions and other physical characteristics related to the embodiments or aspects disclosed herein are not to be considered as limiting.

As used herein, the term "cannabis concentrate" refers to a material containing at least one cannabinoid and/or at least one terpene. A cannabis concentrate may include, for example, a material extracted from a cannabis plant (e.g., via distillation, hydrocarbon extraction, hypercritical $CO_2$ extraction, mechanical extraction, water and/or ice extraction, dry sift separations, heat/pressure extraction, and/or the like) or isolated from the cannabis plant in any way. A cannabis concentrate may include other materials, such as plant waxes and lipids, botanically-derived terpenes that correspond to cannabis terpenes, moisture, and/or the like.

The term "cannabinoid," as used herein, refers to one or more compounds found in the cannabis plant or derived therefrom, such as tetrahydrocannabinolic acid (THCA), cannabidiolic acid (CBDA), tetrahydrocannabinol (THC, THC-Delta 9, THC-Delta 8, etc.), cannabidiol (CBD), tetrahydrocannabivarin (THCV), cannabichromene (CBC), cannabigerolic acid (CBGA), cannabigerol (CBG), cannabinol (CBN), cannabinolic acid (CBNA), and/or the like. A cannabinoid may include a cannabinoid derived from a naturally-occurring cannabinoid, such as CBDA being decarboxylated into CBD, CBD being isomerized into THC, and/or the like. A cannabinoid may also include a synthetic cannabinoid that is not directly derived from the cannabis plant.

The term "terpene," as used herein, refers to one or more hydrocarbons found in the cannabis plant and other plants or derived therefrom. The term "terpene" may refer to both terpenes and terpenoids, which is a modified terpene. Terpenes may include, for example, limonene, pinene, humulene, terpinolene, linalool, geraniol, ocimene, nerolidol, myrcene, and many others.

Figure 2:
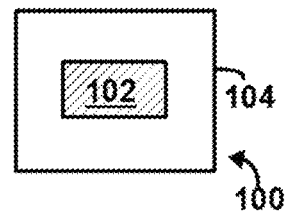
FIG. 2 is a diagram of a vaporization tablet according to a non-limiting embodiment.

Referring to FIGS. 1 and 2, in non-limiting embodiments a tablet 100 includes an inner core 102 and an outer layer 104. At least one of the inner core 102 and outer layer 104 may include one or more cannabinoids. At least one of the inner core 102 and outer layer 104 may include one or more terpenes. The thickness of the outer layer 104 may be variable or uniform. Non-limiting embodiments may utilize different ratios of an amount of outer layer 104 to an amount of inner core 102.

In non-limiting embodiments, the outer layer includes a first cannabis concentrate including crystalized and/or powdered THCA and/or CBDA and/or some other cannabinoid in solidified form. Cannabinoids in the form of an acid, such as THCA, CBDA, CBGA, and the like, are solidified in their natural state at room temperature in the form of crystals and/or powder (e.g., dust) from pulverized crystals. The inner core 102 may include a cannabis concentrate with one or more terpenes, such as a shatter, budder, resin, sauce, rosin, and/or other like terpene-including cannabis concentrates. Such terpene-including cannabis concentrates may be extracted from dry or fresh/frozen cannabis plant matter (e.g., flower and/or leaves). The inner core 102 may also include cannabinoids that have been fully or partially decarboxylated (e.g., THC, CBD, CBG, CBN, etc.) and are viscous. Because such cannabis concentrates may be malleable and adhere to a user's fingers or tools, the outer layer 104 provides a drier and firmer surface that can be picked up and manipulated easily. The outer layer 104 may include a dry cannabis concentrate, such as cannabinoids THCA and/or CBDA. The outer layer 104 may be substantially free of terpenes but, in some non-limiting embodiments, may include any number of dry flavorings.

In non-limiting embodiments, the outer layer 104 may be crystalized THCA and/or CBDA. In some non-limiting embodiments, crystalized cannabinoids may be powdered and formed around the inner core 102 to create the outer layer 104. The powdered cannabinoids may adhere to a surface of the inner core 102 and, in some examples, may be pressed with a tablet pressing device. In some examples, an amount of heat (e.g., 100-180 degrees F.) and/or pressure may be applied to the powdered cannabinoids for one or several seconds to partially melt the cannabinoids to form a compact unitary surface. In some non-limiting embodiments, the cannabinoids for the outer core 104 may be warmed to a temperature (e.g., 100-180 degrees F.) at which it is malleable and formed around the inner core 102 while still malleable. In some non-limiting embodiments, THCA and/or CBDA is crystalized around the inner core 102 by placing an inner core 102 in a solution comprising THCA and/or CBDA and evaporating the solution to form a crystalline outer layer surrounding the inner core 102. The solution may include, for example, water, alcohol, a hydrocarbon solvent, and/or the like.

In non-limiting embodiments, the outer layer 104 may be a dry cannabis concentrate, such as dry sift hash, ice/cold water hash, crumble hash extracted with a hydrocarbon solvent, and/or the like. In such examples, trichomes (e.g., resin glands) may be removed from cannabis plant matter by agitating the matter and sifting the resin glands through filters having various levels of porousness. Full-melt concentrate (e.g., cannabis concentrate that completely vaporizes without leaving significant residual material) may be obtained using filters having pours 73-90μ or smaller. As with pure powdered cannabinoids, the dry cannabis concentrate may be pressed, pressurized, and/or heated to form an outer layer around the inner core. As an example, a piece of cannabis concentrate (such as a small ball or cube of shatter) may be coated in a layer of powdered, dry cannabis concentrate such that the dry extract adheres to the shatter or other type of extract used for the inner core. In some examples, a piece of cannabis concentrate may be coated in another cannabis concentrate that has adhesive properties (e.g., viscous), such as THC and/or CBD oil extracted via $CO_2$, distillation, and/or the like. In some examples, a piece of cannabis concentrate for an inner core may be chilled or frozen before the outer core is formed around it.

In non-limiting embodiments, the outer layer 104 is a firm shell formed from a material that can be handled without significantly softening and that can vaporize completely. As described above, such material may include cannabinoids in solid form, such as THCA and/or CBDA isolate. The material in some non-limiting embodiments may not include any cannabinoids. As an example, a material such as 1-Octadecanol may be used. The material may be any material that can be vaporized and, in non-limiting embodiments, includes any material that has a melting point greater than 100-120 degrees F. and a boiling point below 600 degrees F.

In some non-limiting embodiments, the outer layer 104 may be a firm shell formed from a material that can be handled without significantly softening and that does not vaporize completely, but rather leaves a husk or residue that can easily be removed from a vaporizer. For example, the outer layer 104 may be a thin sheet of plant-based fiber, such as but not limited to hemp, wood pulp, or the like. In other examples, the outer layer 104 may be a metal or ceramic mesh that contains cannabis concentrates but allows vapor to escape. In such embodiments, the inner core 102 may be vaporized while leaving the outer layer 104, and the outer layer 104 may be porous such that the vapor from the inner core 102 passes through it.

FIGS. 1 and 2 show non-limiting embodiments with different ratios of quantities for the inner core 102 as compared to the outer layer 104. The tablet 100 shown in FIG. 1 may have a majority of vaporizable material in the inner core 102, such as a cannabis concentrate including terpenes, and the outer layer 104 may be a lesser amount of material, such as THCA, CBDA, and/or any other solid material that can be handled. The tablet 100 shown in FIG. 2 by contrast has a greater amount of material in the outer layer 104 than in the inner core 102. The inner core 102 in such examples may include terpenes or other flavoring material and the outer layer 104 may include solid cannabinoids or some other firm material.

Figure 3:
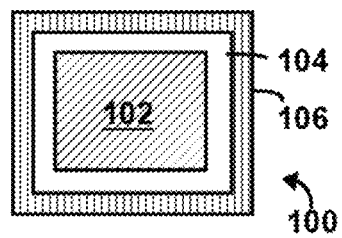
FIG. 3 is a diagram of a vaporization tablet according to a non-limiting embodiment.

FIG. 3 shows a non-limiting embodiment in which a surface layer 106 surrounds the outer layer 104. Thus, the outer layer 104 is arranged outside the inner core 102 but is encapsulated by a further layer 106 that forms a surface that can be touched and manipulated. In such examples, any one of the layers may include cannabinoids and/or terpenes. For example, the inner core 102 may include a first cannabis concentrate, the outer layer 104 may include a second cannabis concentrate that has adhesive properties, such as oil, and the surface layer 106 may include a third cannabis concentrate that is dry, such as powdered and/or crystalized THCA and/or CBDA.

In non-limiting embodiments, the inner core and/or the outer layer may include a predetermined dose of cannabinoids. For example, the inner core and/or outer layer may include between 0.02 and 0.1 grams of a cannabis concentrate. As another example, the dose of the inner core and/or outer layer may be based by the cannabinoid content of the inner core and/or outer layer, such as between 5 and 100 milligrams of a cannabinoid. Additionally or alternatively, the inner core may include a predetermined dose of terpenes.

In non-limiting embodiments, the outer layer is substantially free of terpenes. In some non-limiting embodiments, a terpene content of the outer layer may be less than 1% by weight, less than 0.5% by weight, or the like. In some non-limiting embodiments, a terpene content of the inner core may be greater than 1% by weight. For example, a terpene content may be greater than 1% by weight, greater than 2% by weight, greater than 5% by weight, or the like.

In non-limiting embodiments, a vaporization tablet may be produced by measuring a plurality of doses of cannabinoids and/or terpenes for the inner core and/or outer core. This may include filling molds with a cannabis concentrate and hardening the concentrate with cold temperatures (e.g., 40 degrees or less) to be removed from the molds. Alternatively, an extruding device may be used to obtain inner cores having predefined shapes. Alternatively, a cannabis concentrate may be hardened and cut with a device into pieces that may be used as an inner core. Various other arrangements are possible.

In non-limiting embodiments, a product may include a plurality of vaporization tablets in a container for ease of use. In some examples, the vaporization tablets in a container may each have a substantially similar dose of cannabinoids and/or terpenes. In some examples, a first subset of vaporization tablets in a container may have an inner core with a first set of terpenes and a second subset of vaporization tablets may have an inner core with a second set of terpenes. The first set of terpenes may be associated with a first cannabis strain, for example, and the second set of terpenes may be associated with a second cannabis strain. In this manner, a user may choose between different flavors and/or effects by choosing a different tablet. In some non-limiting embodiments, a first subset of vaporization tablets in a container may have an inner core and/or outer core with a first cannabinoid profile (e.g., one or more cannabinoids) and a second subset of vaporization tablets may have an inner core and/or outer core with a second cannabinoid profile (e.g., one or more cannabinoids differing from the first cannabinoid profile in type of cannabinoid and/or ratio of cannabinoid). The first cannabinoid profile may be associated with a first cannabis strain and the second cannabinoid profile may be associated with a second cannabis strain.

Figure 4A:
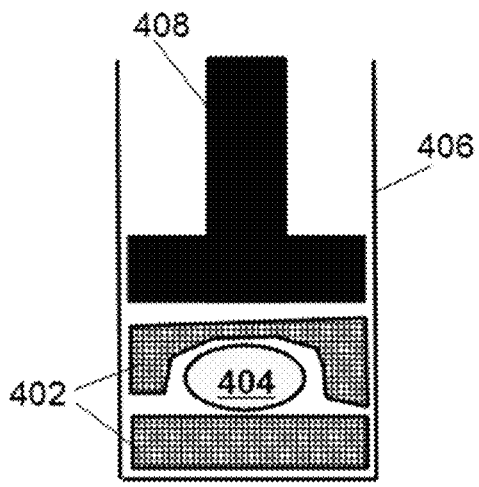
FIGS. 4A and 4B are diagrams of a device for making a vaporization tablet according to a non-limiting embodiment.
Figure 4B:
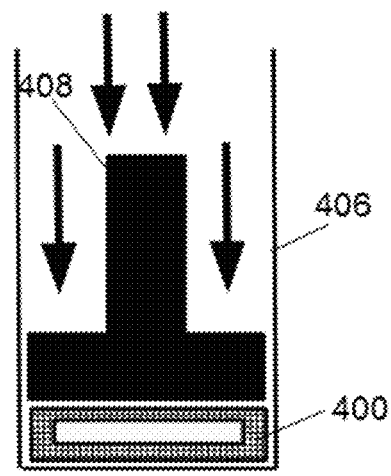

FIGS. 4A and 4B show a non-limiting arrangement for producing vaporization tablets 400. A container 406 holds a layer of a first cannabis extract 402, a second cannabis extract 404 placed on top of the first extract 402, and more of the first cannabis extract 402 placed on top of the second cannabis extract 404. A pressing device 408, such as a piston having an end surface as wide as the container 406, is moved downward to compress the first cannabis extract 402 around the second cannabis extract 404 and to firm a tablet 400. In some non-limiting examples, the container 406 and/or pressing device 408 may be heated.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A tablet for vaporization, comprising:
   an inner core comprising a first cannabis concentrate, the first cannabis concentrate comprising at least one terpene; and
   an outer layer forming a shell around the inner core and fully surrounding the inner core, the outer layer comprising a second cannabis concentrate, the second cannabis concentrate substantially free of terpenes, the outer layer comprising at least 95% by weight of at least one cannabinoid in solid form, the second cannabis concentrate having a firmer consistency than the first cannabis concentrate.

2. The tablet of claim 1, wherein the first cannabis concentrate further comprises one or more cannabinoids.

3. The tablet of claim 1, wherein at least one of the first cannabis concentrate and the second cannabis concentrate comprises a predetermined dose of the at least one cannabinoid.

4. The tablet of claim 1, the second cannabis concentrate comprising at least one of tetrahydrocannabinolic acid and cannabidiolic acid.

5. The tablet of claim 4, wherein the outer layer is crystalized.

6. The tablet of claim 4, wherein the outer layer comprises compressed crystals and/or powder of tetrahydrocannabinolic acid and/or cannabidiolic acid.

7. The tablet of claim 4, wherein a terpene content of the outer layer is less than 1% by weight, and wherein a terpene content of the inner core is greater than 1% by weight.

8. The tablet of claim 7, wherein the outer layer consists of at least one of tetrahydrocannabinolic acid and cannabidiolic acid.

9. The tablet for vaporization of claim 1, wherein the outer layer adheres to a surface of the inner core.

10. A tablet for vaporization, comprising:
    an inner core comprising a first cannabis concentrate, the inner core having a terpene content greater than 1% by weight; and
    an outer layer encapsulating the inner core, the outer layer comprising at least 95% by weight of at least one cannabinoid, the outer layer fully surrounding the inner core.

11. The tablet of claim 10, wherein the terpene content of the inner core comprises at least one terpene.

12. The tablet of claim 11, wherein the at least one cannabinoid of the outer layer comprises at least one of tetrahydrocannabinolic acid and cannabidiolic acid.

13. The tablet of claim 10, wherein the first cannabis concentrate comprises a predetermined dose of the at least one cannabinoid.

14. The tablet of claim 10, wherein the outer layer is drier than the inner core.

15. The tablet for vaporization of claim 10, wherein the outer layer adheres to a surface of the inner core.

16. A product comprising a plurality of tablets, each tablet comprising:
    an inner core having a terpene content greater than 1% by weight; and
    an outer layer fully surrounding the inner core and having a substantially uniform thickness, the outer layer firmer than the inner core and comprising at least 95% by weight of at least one cannabinoid having a boiling point less than 600 degrees Fahrenheit, the outer layer having less than 1% terpene content by weight.

17. The product of claim 16, wherein each tablet is substantially spherical.

18. The product of claim 16, wherein the inner core of each tablet comprises a first cannabis concentrate.

19. The product of claim 16, wherein the outer layer consists essentially of the at least one cannabinoid in acidic form.

20. The product of claim 16, wherein a first subset of the plurality of tablets comprise an inner core including a first set of terpenes, and wherein a second subset of the plurality of tablets comprise an inner core including a second set of terpenes.

* * * * *